United States Patent [19]

Miles

[11] Patent Number: 4,540,406

[45] Date of Patent: Sep. 10, 1985

[54] ANTICOAGULANT DELIVERY SYSTEM FOR USE WITH AN AUTO-TRANSFUSION SYSTEM

[75] Inventor: Clive Miles, Oakland, Calif.

[73] Assignee: Thoratec Laboratories Corporation, Berkeley, Calif.

[21] Appl. No.: 490,675

[22] Filed: May 2, 1983

[51] Int. Cl.³ .............................................. A61M 5/00
[52] U.S. Cl. ................................. 604/269; 604/902; 604/4; 604/119
[58] Field of Search ............... 604/4, 73, 119, 120, 604/141, 246, 269, 902; 137/888

[56] References Cited

U.S. PATENT DOCUMENTS

| Re. 29,346 | 8/1977 | Kopp | 128/214 R |
|---|---|---|---|
| 2,032,614 | 3/1936 | Guiou | 128/214 |
| 2,449,497 | 9/1948 | McLeod | 128/276 |
| 2,689,565 | 9/1954 | Gobel | 128/214 |
| 2,697,435 | 12/1954 | Ray | 128/214 |
| 2,804,075 | 8/1957 | Borden | 128/276 |
| 2,935,068 | 5/1960 | Donaldson | 128/348 |
| 2,988,001 | 6/1961 | D'Arcey et al. | 103/4 |
| 3,191,600 | 6/1965 | Everett | 128/276 |
| 3,452,751 | 7/1969 | Austin | 128/277 |
| 3,463,159 | 8/1969 | Heimlich | 128/350 |
| 3,595,234 | 7/1971 | Jackson | 128/276 |
| 3,623,483 | 11/1971 | Dyer | 128/276 |
| 3,680,560 | 8/1972 | Pannier et al. | 128/276 |
| 3,704,709 | 12/1972 | Sorenson et al. | 128/277 |
| 3,719,197 | 3/1973 | Pannier et al. | 137/205 |
| 3,802,432 | 4/1974 | Djerassi | 128/214 R |
| 3,807,401 | 4/1974 | Riggle et al. | 604/902 |
| 3,853,126 | 12/1974 | Schulte | 128/214 R |
| 3,863,634 | 2/1975 | Reynolds et al. | 128/276 |
| 3,866,608 | 2/1975 | Reynolds et al. | 128/276 |
| 3,955,573 | 5/1976 | Hansen et al. | 128/276 |
| 3,964,484 | 6/1976 | Reynolds et al. | 604/269 |
| 3,965,896 | 6/1976 | Swank | 128/214 R |
| 3,989,046 | 11/1976 | Pannier et al. | 128/276 |
| 4,006,745 | 2/1977 | Sorenson et al. | 128/214 R |
| 4,033,345 | 7/1977 | Sorenson et al. | 128/214 R |
| 4,047,526 | 9/1977 | Reynolds et al. | 128/214 R |

FOREIGN PATENT DOCUMENTS 2605005  9/1976  Fed. Rep. of Germany ...... 604/902

OTHER PUBLICATIONS

"Intraoperative Autotransfusion", Bennett et al., American Journal of Surgery, vol. 123, pp. 257-260, Mar. 1972.
"Hematologic Integrity After Intraoperative Allotransfusion", Aaron et al., Arch. Surg., vol. 108, pp. 831-837, Jun. 1974.
"A Simple Method of Intraoperative Autotransfusion", Noon et al., Surgery, Gynecology and Obstetrics, vol. 143, pp. 65-70, Jul. 1976.
"Receptal ATS Mediastinal", Published by Sorenson Research Co., P. O. Box 15588, Salt Lake City, Utah 84115, 4/78-S1390-8 pages.
"Receptal ATS Trauma", Published by Sorenson Research Co., P.O. Box 15588, Salt Lake City, Utah 84115 1/79-S1220-8 pages.
"The Graphic Languages of Engineering", Steidel and Henderson, Published by John Wiley & Sons Co., 1983, p. 13, Fig. 1.7.

Primary Examiner—C. Fred Rosenbaum
Assistant Examiner—J. L. Kruter
Attorney, Agent, or Firm—Flehr, Hohbach, Test, Albritton & Herbert

[57] ABSTRACT

Anticoagulant is added to blood being aspirated through a hand-held wand having a venturi throat. The anticoagulant flows into the wand from a generally closed anticoagulant reservoir higher than the wand as replacement air flows into the anticoagulant air reservoir. This air inflow is controlled by a regulator fixed on the wand and in accordance with the amount of aspirated blood flowing in through the venturi throat.

8 Claims, 1 Drawing Figure

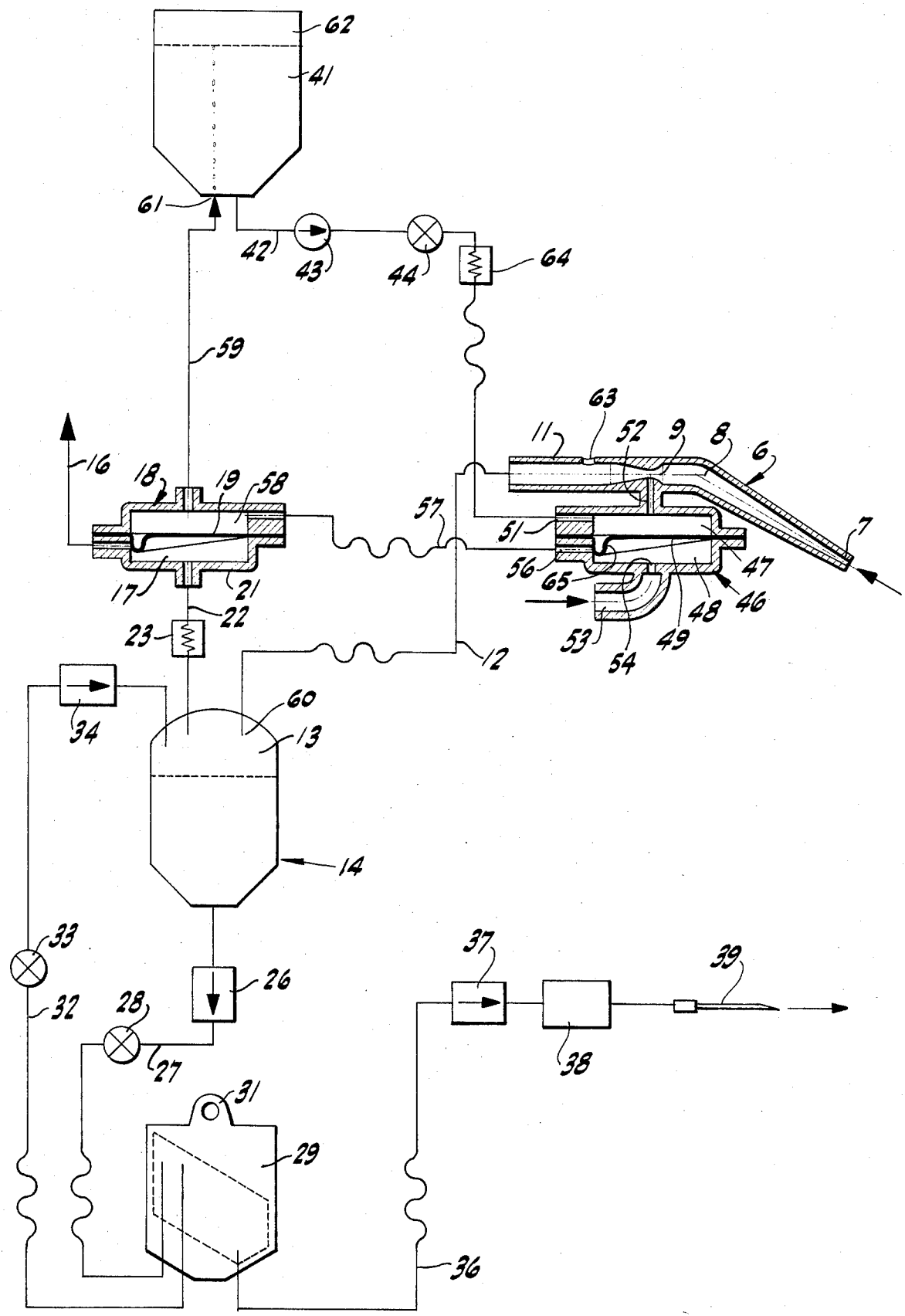

ANTICOAGULANT DELIVERY SYSTEM FOR USE WITH AN AUTO-TRANSFUSION SYSTEM

CROSS-REFERENCES TO RELATED APPLICATIONS

My application entitled "Pressure Regulator" filed May 2, 1983 with Ser. No. 490,674 shows a structure of the general kind disclosed herein, the application of Clive Miles and Gary Schneiderman entitled "Autotransfusion System With Anticoagulant Delivery System" filed May 2, 1983 with Ser. No. 490,673 discloses a related system for delivering anticoagulant, and the application of Robert H. Bartlett entitled "Autotransfusion System" filed Mar. 7, 1983 with Ser. No. 472,763 discloses an autotransfusion system employing a similar method of blood handling.

BACKGROUND OF THE INVENTION

The invention relates to means for the use of an anticoagulant in connection with autotransfusion of blood. Customarily, an intraoperative autotransfusion system includes a suction wand for aspirating blood from an open wound site, a blood reservoir for collecting the aspirated blood and a flexible conduit for conducting the blood from the wand to the reservoir. To prevent clotting of the aspirated blood, it is often desirable to add an effective anticoagulant to the blood as, or promptly after, it is aspirated. The desirable proportion of anticoagulant to blood is generally fixed within a specific range. Anticoagulant can be added through a side port of the wand into a blood flow passageway or lumen where it mixes with the blood as it flows through the wand during aspiration. Commonly, a tube connects the site of anticoagulant entry at the wand with a source of anticoagulant positioned at a particular, generally remote and fixed height.

As discussed in the copending application of Clive Miles and Gary Schneiderman entitled "Autotransfusion System With Anticoagulant Delivery System", the delivery of anticoagulant to the blood depends in part on the height at which the wand is operated (i.e., the height of the wound site) relative to the height location of the anticoagulant source. This is because the driving force for anticoagulant delivery from the anticoagulant source to the blood flowing through the wand generally depends upon several factors, including the hydrostatic head of anticoagulant associated with the height difference between the anticoagulant source and the site of anticoagulant entry into the wand. A change in the operating elevation of the wand relative to the anticoagulant source may therefore affect the driving force for anticoagulant, thus altering the proportion of anticoagulant to blood so that the desired range of said proportion may be exceeded.

The anticoagulant system described herein is particularly designed to compensate for the effects of changes in the aspirating wand elevation relative to the anticoagulant source. The system utilized in the present disclosure represents an improvement over the structure disclosed in the aforementioned copending application of Clive Miles and Gary Schneiderman.

BRIEF SUMMARY OF THE INVENTION

An automatic anticoagulant delivery system especially for use in an autotransfusion system has a suction wand supplied with anticoagulant from an anticoagulant container or source disposed at a relatively high location above the useful positions of the wand. An anticoagulant control device or tank is fixed on the wand and is divided by a flexible separator or diaphragm into two chambers.

As blood is aspirated and flows through the wand, a hydrodynamic suction draws anticoagulant from the first of said tank chambers into the blood flowing through the wand. This results in a movement of said flexible diaphragm which allows atmospheric air to be drawn into the second of said chambers and to flow through a tube into the remote anticoagulant container. This air flow to the container allows anticoagulant to flow from the anticoagulant container, through a tube and into the first of said tank chambers which is automatically refilled thereby.

The invention is thus effective to provide a device or tank for anticoagulant which is mounted on, and "rides" with, the suction wand and communicates with the blood flow passageway of the suction wand through a port. The anticoagulant in this tank is maintained at (or near) atmospheric pressure and is automatically refilled from a remote source or container. Thus, although the operating height of the wand relative to the anticoagulant container may change with circumstance, anticoagulant at or near atmospheric pressure is always available to be drawn into the aspirated blood.

PRIOR ART OF INTEREST

Patents

| | | | |
|---|---|---|---|
| 2,032,614 | Guiou | 3,719,197 | Pannier et al. |
| 2,449,497 | McLeod | 3,802,432 | Djerassi |
| 2,689,565 | Gobel | 3,807,401 | Riggle et al. |
| 2,697,435 | Ray | 3,853,126 | Schulte |
| 2,804,075 | Borden | 3,863,634 | Reynolds et al. |
| 2,935,068 | Donaldson | 3,866,608 | Reynolds et al. |
| 2,988,001 | D'Arcy et al. | 3,955,573 | Hansen et al. |
| 3,191,600 | Everett | 3,965,896 | Swank |
| 3,452,751 | Austin | 3,989,046 | Pannier et al. |
| 3,463,159 | Heimlich | 4,006,745 | Sorenson et al. |
| 3,492,991 | Dyer | 4,014,329 | Welch et al. |
| 3,595,234 | Jackson | 4,033,345 | Sorenson et al. |
| 3,623,483 | Dyer | 4,047,526 | Reynolds et al. |
| 3,680,560 | Pannier et al. | Re. 29,346 | Kopp |
| 3,704,709 | Sorenson et al. | | |

Publications

Hematologic Integrity After Intraoperative Allotransfusion, Aaron et al., Arch. Surg/Vol 108, June 1974

Intraoperative Autotransfusion, Bennett et al., The American Journal of Surgery - Vol. 123, pgs. 257–260, 1972

Receptal ® ATS Mediastinal - 4/78 - S1390, Published by Sorenson Research Co., P. O. Box 15588, Salt Lake City, Utah Receptal ® ATS Trauma - 1/79 - S1220, Published by Sorenson Research Co., P. O. Box 15588, Salt Lake City, Utah A Simple Method of Intraoperative Autotransfusion, Noon et al., Surgery, Gynecology and Obstetrics - Vol. 143, pgs. 65–70, 1976

The Graphic Languages of Engineering, Steidel and Henderson, John Wiley & Sons, 1983, Page 13, FIG. 1.7

BRIEF DESCRIPTION OF THE DRAWING

The FIGURE is a diagram, with certain portions in cross-section, showing an anticoagulant delivery system as used with an autotransfusion system.

DETAILED DESCRIPTION

In an autotransfusion system of the sort represented in the above-identified application of Robert H. Bartlett, anticoagulant is drawn into a suction wand that aspirates the blood from the patient. This is so that the aspirated blood will not clot in the autotransfusion system prior to its return to the patient. The amount of anticoagulant that can properly be added lies within a relatively limited range. The amount added is affected by the movement of the wand higher and lower as blood may be aspirated from locations at different heights.

To accomplish the desired, admixture of anticoagulant to the aspirated blood, to do so in all desired positions of the movable wand and without exceeding the desired ratios of anticoagulant to blood, and to do so with a relatively simple, straightforward, reliable mechanism, there is provided an arrangement for treatment of a patient lying at a particular elevation. His blood is aspirated from any available pools through a wand 6 movable between various different elevations and in various orientations. The hand-held wand has an inlet 7 leading into an interior passageway 8 and discharging through an integral handle 11 into a line 12 extending to the upper portion 13 or upper space of a blood reservoir 14. Preferably, the passageway 8 includes a venturi shape 9 or throat. The reservoir 14 is subjected to vacuum from a remote vacuum source 16 leading through one chamber 17 of a vacuum regulator 18 of the sort disclosed in the Miles application above identified, and vacuum regulation being effected by means of a flexible diaphragm 19 arrangement. The diaphragm 19 divides the regulator 18 and provides a chamber 17 partly defined by a wall 21 and connected through a conduit 22, an air flow restriction 23, and finally opening into the reservoir space 13. Vacuum under the control of the vacuum regulator is thus available to induce aspiration of blood into the wand 6 through the tip 7.

Preferably, as in many conventional hand-held suction wands, there is an opening 63 which communicates the hollow interior or blood flow passageway of the wand 6 with the atmosphere. The system operator uses a finger to cover the opening 63 to cause said vacuum in the space 13 to be effective at the wand tip 7 to initiate and maintain blood aspiration, or to uncover the opening 63 to stop blood aspiration.

Pursuant to the present invention, the anticoagulant delivery system is set up and used as follows. A container 41 is initially upright and filled with anticoagulant except for an air space at atmospheric pressure. The container is then connected to lines 59 and 42, using appropriate means, and then inverted as shown in FIG. 1. The anticoagulant container 41 is then supported at a fixed, predetermined location above a blood entry point 60 into the reservoir 14. As described below (also see the above-referenced copending application by Clive Miles and Gary Schneiderman), it is the vertical distance between an entry point 61 into the container 41 and the blood entry point 60 which sets the net driving force for blood aspiration from the wand tip 7 to the blood reservoir space 13. The positioning of the anticoagulant container 41 and blood reservoir 14 must be such that the point 61 is somewhat above the uppermost point at which the wand 6 will be operated.

During initial priming, a shut-off clamp 44 is opened and anticoagulant outflow by gravity is used to fill the line 42, a chamber 47 and a line or passageway 52. This outflow results in the establishment of a partial vacuum in a space 62 which is effective on the air/liquid interface in the container 41. During this priming, anticoagulant continues to flow out of the container 41 by gravity until the vacuum level in the space 62 increases sufficiently to hold up the gravity head of the anticoagulant in the container 41, line 42 and chamber 47. Preferably, the line 42 and chamber 47 are filled by this priming process. As described in the above-referenced Miles and Schneiderman application, the vacuum regulator 18 provides a vacuum level available in the space 13 of the reservoir 14 which substantially corresponds with the pressure sensed through the line 59 at the point 61. Thus, the vacuum level at which the regulator 18 regulates varies with relative changes in elevation between the wand 6 and the reservoir 14 (if the container 41 remains fixed relative to the reservoir 14). As discussed in the above-referenced copending application by Miles and Schneiderman, this apparatus thereby compensates for variations in relative elevation between the wand 6 and reservoir 14.

The container 41 has a discharge line 42 leading through a check valve 43, an on/off valve 44, and an optional flow restriction 64 into an anticoagulant tank 46 mounted on the wand. The tank 46 is somewhat comparable to the regulator disclosed in the above-identified Miles application entitled "Pressure Regulator" and includes a first chamber 47 for anticoagulant and a second chamber 48. These are divided by a diaphragm 49 having a peripheral flexible rolling convolution 65. Anticoagulant from the chamber 47 can flow through a conduit or passageway 52 opening into the throat 9 of the venturi section of the wand. The normal "resting" position of the diaphragm 49 is such that its peripheral, convoluted portion 65 covers and obstructs the opening of a passage 56 into the chamber 48. The opening is circular, rectangular or otherwise characterized. The passage 56 leads to a flexible line or conduit 57 open to the chamber 58 of the regulator 18. This chamber leads through the line 59 to the anticoagulant container 41. Through a passage 53 and restricting orifice 54, the chamber 48 communicates with the atmosphere.

In operation, with the hole 63 closed, vacuum from the space 13 draws blood through the venturi 9 of the wand to flow into the blood reservoir 14 for disposition as described below. This blood flow creates a hydrodynamic suction effective at the opening of the passage 52 into the wand, tending to draw anticoagulant from the chamber 47 into the blood flowing through the venturi 9 for mixing therewith. The flexibility of the peripheral convolution of the diaphragm allows the anticoagulant to flow out of the chamber 47 as the diaphragm 49 moves up (as shown in the FIGURE) to reduce the volume of the chamber 47. As the diaphragm rises, its flexible edge rises and uncovers part or all of the passage 56, thus allowing atmospheric air to be drawn from the chamber 48, through the line 57, the chamber 58, and the line 59 into the anticoagulant container 41. Air entering the bottom of the container 41 bubbles up through the anticoagulant and into the space 62, thus reducing the vacuum level (increasing the pressure) therein. With the pressure change, anticoagulant is thereby released from the container 41 to flow through the line 42 and the passage 51 into the chamber 47, which is thus automatically refilled. When blood aspiration is stopped, anticoagulant ceases to be drawn from the chamber 47, the chamber 47 refills, and the diaphragm 49 returns to its "resting" position in which the air passageway 56 is covered and sealed by the diaphragm edge 65 such that air can no longer flow up to the container 41. Under these conditions, the anticoagulant flow to the chamber 47 will be completely or nearly stopped. However, in practice, some small amount of anticoagulant may continue to flow from the container 41 until the vacuum level in the space 62 is large enough to offset the hydrostatic head of anticoagulant between the free surface of anticoagulant in the container 41 and the effective head of anticoagulant in the tank 46. In this way, the effects of variations in elevation between the wand and the anticoagulant source are substantially eliminated.

In practice, the performance of the device under various conditions (including aspiration of air along with the blood) may be adjusted as desired through choice of various design parameters, including: the magnitude of the flow resistances afforded by the passage 54, the restriction 23, and by an anticoagulant passage 52 and the flow restriction 64; and the amount of flexibility vs. stiffness of movement of the diaphragm 49, as determined by its geometry and by the thickness and physical properties of its material.

The anticoagulant delivery system of the present invention includes the anticoagulant tank fixed on the suction wand, and specific means for automatic refilling from a remote source, and for minimizing the effects of changes in the operating height of the wand relative to the remote source. This system may be appropriate for use with various types of means for handling the aspirated blood after being anticoagulated. A specific means for blood handling is shown in the FIGURE.

In the operation of this blood handling part of the structure, the blood is aspirated by and through the wand, where it receives anticoagulant, and is deposited through the line 12 into the lower part of the reservoir 14. From the reservoir 14, flow is through a check valve 26 in a line 27 having a shut-off valve 28 therein and extending into a flexible or collapsible blood bag 29. A tab 31 on the bag permits the bag to be disposed in a low position (below the reservoir 14), as shown in the drawing, or to be lifted to a high position at an elevation above that of the patient. The low position is used for filling the blood bag 29 by gravity from the reservoir 14. The high position is used for delivery of blood from the blood bag 29 to the patient. There is a blood bag de-airing line 32 with a control valve 33 and a check valve 34 therein extending between the upper portion of the bag 29 and the reservoir space 13 so that air entrained with the blood in the bag 29 may readily be caused to separate from the blood by buoyancy and to flow through the line 32 to the space 13 of the reservoir 14. Blood from the bag 29, when the bag is elevated, flows through a flexible conduit 36 and through a check valve 37 and a filter 38 into an infusion needle 39. In this way blood that has been taken from the patient through the wand is transferred appropriately for reintroduction through the needle 39. As an elective alternative, the blood from the bag 29 may be directed to flow to a standard blood bag for storage, or to a standard blood processing device or cell washing device for processing, rather than to the patient.

I claim:

1. An automatic anticoagulant control for an autotransfusion system comprising an anticoagulant container disposed at a predetermined altitude, a suction wand having a passageway for flow therethrough and operable between various altitudes below said predetermined altitude, a hollow control body fixed on and movable with said wand, a diaphragm movable into different positions and dividing said control body into a first chamber and a second chamber, means defining a passage extending between said wand passageway and said first chamber, means for conducting anticoagulant from said anticoagulant container to said first chamber, means for admitting air to said second chamber, a port in said second chamber variably obscured by said diaphragm in said different positions thereof, and means including said port for conducting air from said second chamber to said anticoagulant container.

2. A device as in claim 1 in which said admitted air is from the atmosphere.

3. A device as in claim 2 including means for restricting the flow of said atmospheric air into said second chamber.

4. A device as in claim 1 including a source of vacuum, a flexible conduit connecting said source of vacuum and said suction wand, said means for conducting anticoagulant from said anticoagulant container to said first chamber including another flexible conduit and said means for conducting air from said second chamber to said anticoagulant container including still another flexible conduit.

5. An automatic anticoagulant control comprising a suction wand having an internal passage, means for admitting blood to one end of said passage, means for connecting the other end of said passage to a source of vacuum, a hollow control body fixed on said wand, a movable diaphragm dividing said control body into a first chamber and a second chamber and movable into different positions, means defining a passage extending between said internal passage and said first chamber, means for admitting anticoagulant to said first chamber, means for admitting air to said second chamber, and a port in a wall of said second chamber variably obscured by said diaphragm in said different positions thereof for controlling flow of said admitted air from said second chamber.

6. A device as in claim 5 in which said internal passage includes a venturi shape.

7. A device as in claim 6 in which said means defining a passage extending between said internal passage and said first chamber communicates with said internal passage at said venturi throat.

8. A device as in claim 1 in which said passageway for flow therethrough includes a venturi shape and in which said means defining a passage extending between said passageway and said first chamber communicates with said passageway at said venturi throat.

* * * * *